United States Patent [19]

Scherrer et al.

[11] 4,231,965

[45] Nov. 4, 1980

[54] PHENOXY PHENYL ETHANONES

[75] Inventors: Robert A. Scherrer, White Bear Lake; Richard M. Stern, Cottage Grove, both of Minn.

[73] Assignee: Riker Laboratories, Inc., Northridge, Calif.

[21] Appl. No.: 17,816

[22] Filed: Mar. 5, 1979

Related U.S. Application Data

[62] Division of Ser. No. 943,690, Sep. 19, 1978, Pat. No. 4,154,848, which is a division of Ser. No. 861,893, Dec. 19, 1977, Pat. No. 4,128,659.

[51] Int. Cl.$^2$ .................. C07C 49/84; C07C 65/16
[52] U.S. Cl. .................... 568/327; 562/462; 562/463; 568/328; 568/331
[58] Field of Search ............ 260/590 D, 590 R, 592; 562/463, 402

[56] References Cited

U.S. PATENT DOCUMENTS 3,862,134  1/1975  Scherrer .................. 260/346.2 R

FOREIGN PATENT DOCUMENTS 2543099  4/1976  Fed. Rep. of Germany .... 260/346.2 R

OTHER PUBLICATIONS

Abdushukuror et al, Chem. Abst., vol. 85, #192299d (1976).
Rivalle et al, Bull. Chem. Soc. Fr., 1972 (7) pp. 2750-2755.

*Primary Examiner*—Norman Morgenstern
*Assistant Examiner*—James H. Reames
*Attorney, Agent, or Firm*—Cruzan Alexander; Donald M. Sell; Donald C. Gipple

[57] ABSTRACT

2-Nitrobenzofurans in which the furan ring is either fused to or substituted by a fused bicyclic system, which are active as antimicrobial agents, processes for their use and intermediates therefor are described.

2 Claims, No Drawings

PHENOXY PHENYL ETHANONES

This is a division of copending application Ser. No. 943,690 filed Sept. 19, 1978, now U.S. Pat. No. 4,154,848 which is a division of copending application Ser. No. 861,893 filed Dec. 19, 1977 (now U.S. Pat. No. 4,128,659).

BACKGROUND OF THE INVENTION

The present invention relates to certain substituted 2-nitrobenzofuran compounds which are active antimicrobial agents, to processes for their use and to intermediates in their preparation.

Many 2-nitrofurans and a number of 2-nitrobenzofurans are known, and some of the latter are known to have anti-microbial activity (see, for example, Belgian Pat. No. 846,502 and German Offenlegungsschrift No. P 2642877 which disclose 2-nitrobenzofurans substituted by an alkanoic acid group as having antimicrobial activity). However, 2-nitrobenzofurans in which the furan ring is either fused to or substituted by a fused ring system (as is the case in the present invention) have not been known previously.

DETAILED DESCRIPTION OF THE INVENTION

The compounds of the present invention contain a benzofuran ring system which is either part of a naphthofuran or indenofuran system and contains a 3-phenyl group or contains a 3-naphthyl group.

The invention also relates to pharmaceutically acceptable salts of certain of the compounds, to the use of the compounds and salts as antimicrobial agents and to synthetic intermediates useful for their preparation.

More specifically, the invention relates to compounds of the formula

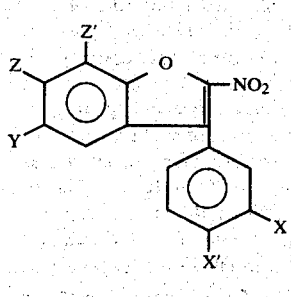

I wherein

X and X' are individually hydrogen, fluorine, chlorine, bromine or carboxyl or together can complete a benzo ring, Y is hydrogen, fluorine, chlorine, bromine, carboxyl, carboxymethyl or, together with Z, can form a propylene chain, Z and Z' are individually hydrogen or together can complete a benzo ring, provided that the compound contains one and only one of the rings including X and X', Y and Z, and Z and Z', and provided further that the compound contains not more than a single carboxyl function, and, when the compound contains a carboxyl function, to pharmaceutically acceptable salts thereof.

The intent of the foregoing (specifically in the second proviso) is that the compounds of formula I contain no more than a single member of the class consisting of carboxyl and carboxymethyl groups (and thus cannot contain two of either or one of each).

The pure compounds of the invention are generally yellow or orange to brown crystalline solids. They are substantially insoluble in water or aliphatic hydrocarbons and are more soluble in acetone, lower alcohols, halogenated solvents, benzene, N,N-dimethylformamide and the like. When salts are prepared, they have appreciable solubility in water and lower alcohols.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents.

The free acids are presently preferred for many purposes due to their generally higher levels of antimicrobial activity in vitro. For applications in which water solubility is of importance, the salts are ordinarily used. Compounds of the invention wherein Z and Z' together complete a benzo ring, i.e. which conform to the formula

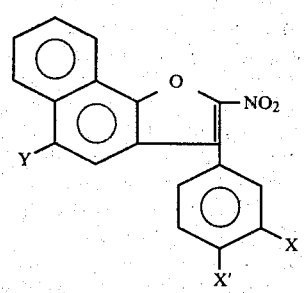

II form another important subclass of the compounds of the invention, particularly the compounds of this type in which X, X' and Y are hydrogen, halogen or carboxyl.

The compounds of the invention are generally prepared by reacting appropriately substituted phenols, naphthols or hydroxyindanes with appropriately substituted α-chloro or α-bromoacetophenones or -naphthones according to the following reaction scheme:

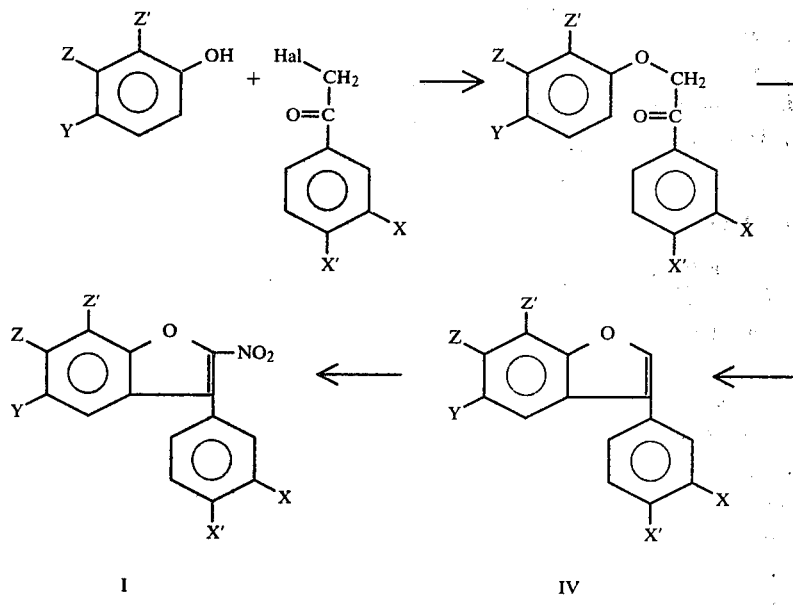

wherein Hal is chloro or bromo and X, X', Y, Z and Z' are as previously defined.

The reaction to prepare the novel intermediate condensation products of formula III is generally carried out at reflux in an inert solvent such as benzene, acetone and the like, in the presence of a weak base such as sodium or potassium carbonate. Increased basicity may be used to increase the rate of reaction, if desired. The condensates III are cyclized by heating in the presence of polyphosphoric acid to form the novel compounds IV.

The compounds of formula IV are converted to the desired 2-nitro compounds (I) either by direct nitration or by halogen displacement, i.e. specifically halogenating (iodinating or brominating) the 2-position of the benzofuran moiety, then replacing the 2-halogen atom with a nitro group employing a nitrating agent.

Compounds of formula IV of the present invention wherein Y, X or X' is chlorine or bromine can be converted to Grignard reagents and reacted with carbon dioxide to provide other compounds of formula IV of the invention wherein Y, X or X' is carbonyl.

The direct nitration of the 2-position of the compounds IV can be carried out with fuming nitric acid in acetic acid or acetic anhydride or with dinitrogen tetroxide in an inert solvent such as dichloromethane. In order to avoid aromatic nitration moderate temperatures of 0° to 30° C. are generally used.

The halogenation step of the halogen displacement process may be bromination or iodination. The bromation can be carried out using N-bromosuccinimide or preferably bromine in a suitable solvent such as dichloromethane or acetic acid. Bromination is carried out under mild conditions, e.g. 0° to 30° C. to avoid aromatic bromination. The bromo compound may be isolated or used without isolation. Isolation may be carried out by extraction, precipitation by the addition of a non-solvent such as water, evaporation of volatile reaction components, etc. The iodination is carried out e.g. with a molecular iodine in the presence of yellow mercuric oxide in an inert solvent such as benzene. Generally these reactions are carried out at about 25° to 125° C., for example at the reflux temperature of the solvent.

In the final step of the halogen displacement process, the 2-halo substituent can be displaced by means of selecting nitrating agents, such as strong nitric acid solution, for example 70 percent aqueous nitric acid, dinitrogen tetroxide in e.g. acetic acid or dichloromethane solution or a mixture of sodium nitrite and a strong acid. When 70 percent nitric acid is used as the nitrating reagent for 2-halo derivatives, preferably about two or three moles each of sodium nitrite and nitric acid per mole of benzofuran is included. About four to twenty milliliters of acetic acid per gram of 2-halobenzofuran derivative is used, depending on its solubility. It is desired to maintain the dissolution of the 2-halobenzofuran derivative, and the amount of acetic acid and the reaction temperature is adjusted to achieve this result readily. The reaction temperature is about 25° to 100° C., and preferably about 60° to 80° C. when the halogen is bromine.

It has been found that a mixture of sodium nitrite, sulfuric acid and acetic acid will also nitrate the 2-halobenzofuran derivatives successfully in the 2-position. The 2-halobenzofuran derivative is dissolved in acetic acid to maintain solution (up to 20 ml. per gram required), and concentrated sulfuric acid is added, from two to ten milliliters per gram of benzofuran. Sodium nitrite is then added to the solution. The reaction temperature is about 20° to 100° C., and preferably about 55° C. The sodium nitrite can be replaced in this reaction by other metal nitrites such as potassium nitrite. In each of the preceding nitration methods, polynitration is a side-reaction.

A combination of nitrogen tetraoxide in an inert solvent in the presence of an alkene is one presently preferred nitration method according to the halogen displacement process, with acetic acid and dichloromethane as the preferred solvents. For example, two to five liters of acetic acid per mole of benzofuran or halobenzofuran derivatives are generally used. At least one mole of nitrogen tetraoxide per mole of benzofuran is used. The exact amount depends on the rate of reaction desired, the extent of volatilization and other physical losses and the amount of competitive addition to the added olefin. An alkene is preferably used with a 2-bromobenzofuran intermediate to remove the elements of $BrNO_2$ and minimize bromination as a side reaction. Cyclohexene is satisfactory for this use. Preferably equimolar amounts of alkene and nitrogen tetraoxide are used. The olefin is chosen to be less reactive to $N_2O_4$ than the benzofuran but more reactive to $BrNO_2$ than the benzofuran. An acidic olefin, e.g. 3-cyclohexene carboxylic acid, is advantageous when the nitrated product is neutral. The temperature of these reactions is generally about 0° to 80° C., preferably 20° to 45° C. for bromine exchange and about 0° to 25° C. for iodine exchange and direct nitration. When 2-iodobenzofurans are used, the olefin is not required (since the iodine is generally unreactive to the benzofuran under the reaction conditions) and only one-half mole of $N_2O_4$ is theoretically then required.

The pharmaceutically acceptable salts of the invention are readily prepared by reaction of the corresponding free acids with the appropriate base and optionally in a suitable solvent and evaporation to dryness. The base used to prepare the salts may be organic, e.g. sodium methoxide or an amine, or inorganic. Furthermore, other salts which are not pharmaceutically acceptable may be useful for the synthesis of the acid compounds or other, acceptable salts.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli, Streptococcus sp.* (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis*.

These are selected representatives of various bacterial and fungal classes and broad spectrum activity can be predicted as a result of activity against them. All of the compounds of the invention possess antimicrobial activity towards one or more of the above microorganisms. The compounds maintain high activity against the microorganisms either in the absence or presence of ten percent horse serum.

The in vivo antimicrobial activity is determined against infections produced by *Streptococcus pyogenes* C-203 and *Staphylococcus aureus* (Smith) or other bacterial species. The species used is determined by the in vitro antimicrobial spectrum of the compound. Groups of five or ten mice, 18–22 g., are infected intraperitoneally with the test culture. Treatment consists of three oral injections one, six and 24 hours after infection. All mice are observed for extended periods, e.g. for two weeks, and deaths are recorded at daily intervals. Control groups consist of one infected, nontreated group and other infected groups receiving varying dosages of the reference standard.

The acute oral toxicity of the compounds of the invention generally is moderate to low compared with the effective oral dose, and they have good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about five parts per thousand are suitable, and the formulation is used by immersing the object to be treated therein, or by local application to an infected area. The amount of compound to be used for treatment of a microbial infection will be an effective amount less than a toxic amount. The amount to administered to a subject and route of administration to control an infection will depend on the species of organism, the sex, weight, physical condition of the subject, the locus of the infection, and many other factors, but this judgment is well within the skill of the art. Usually the amount will be less than 100 mg/kg per dose. Conveniently the oral treatment is administered in the form of the usual pharmaceutical preparations such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

In view of the outstanding antimicrobial activity of the compounds, they would also be expected to be effective growth promoters in various animal and bird species.

The following examples are given for the purpose of further illustrating the procedures of the present invention, but are not intended, in any way, to be limiting on the scope thereof. The melting points are uncorrected, and the temperatures are in degrees Centigrade.

EXAMPLE 1

Step A. A mixture of 26 g. (0.18 mole) of α-naphthol, 50 g. (0.18 mole) of 4,α-dibromoacetophenone, 55.2 g. of sodium carbonate and 300 ml. of dry acetone is heated at its reflux temperature for about one day. The mixture is cooled, filtered and then evaporated to provide a residue which is recrystallized from a dichloromethane-petroleum ether mixture. The product is 4-bromo-α-(α-napthoxy)acetophenone. The structural assignment is supported by infrared and nuclear magnetic resonance spectral analysis.

Step B. The product of step A is mixed with 500 g. of polyphosphoric acid and the mixture is heated at 100° C. for four hours. The mixture is poured into 1 liter of ice water, then filtered. The solid isolated is recrystallized from a chloroformpetroleum ether mixture to provide 3-(4'-bromophenyl)naphtho-[1,2-b]furan, m.p. 125°–130° C.

| Analysis: | %C | %H | |
|---|---|---|---|
| Calculated for C$_{18}$H$_{11}$BrO: | 66.9; | 3.4 | |
| Found: | 66.7; | 3.4. | |

Step C. A solution of 2 g. of the product of step B in 50 ml. of dichloromethane is treated with 2.0 g. of dinitrogen tetraoxide, and the mixture is stirred at about 20° C. for about 18 hours. The mixture is evaporated, and the residue obtained is recrystallized from aqueous ethanol to provide yellow crystals of 3-(4'-bromophenyl)-2-nitronaphtho-[1,2-b]furan, m.p. 230°–233° C.

| Analysis: | %C | %H | %N |
|---|---|---|---|
| Calculated for C$_{18}$H$_{10}$BrNO$_3$: | 58.7; | 2.7; | 3.8 |
| Found: | 58.3; | 2.6; | 3.8. |

EXAMPLE 2

Step A. Using the method of Example 1, step A. starting with α-naphthol and α-bromoacetophenone, the product obtained is α-(α-naphthoxy)acetophenone. The reaction solvent used is benzene. The product is used without further purification for the next step.

Step B. Using the method of Example 1, step B, the product of Example 2, step A, is cyclized in polyphosphoric acid to provide 3-phenylnaphtho-[1,2-b]furan. The product is purified by chromatography on a silica gel column, eluting with carbon tetrachloride. The first fractions are the desired product. The product is recrystallized from hexane to provide a yellow solid, m.p. 98°–109° C. The structural assignment is supported by infrared and nuclear magnetic resonance spectral analysis.

Step C. A solution of 8.4 g. (0.034 mole) of the product of step B in 100 ml. of dichloromethane and 4.1 g. of sodium acetate is treated with 5.4 g. (0.034 mole) of bromine in 30 ml. of dichloromethane. After the dropwise addition is completed, the mixture is stirred for about one hour. The mixture is then washed thoroughly with water and a saturated sodium chloride solution. The organic layer is dried then evaporated to provide a residue which is shown to be 2-bromo-3-phenylnaphtho[1,2-b]furan by infrared and nuclear magnetic resonance spectral analysis.

Step D. A solution of 11 g. (0.034 mole) of the product of step C in 500 ml. of acetic acid and 6.4 g. of cyclohexene-4-carboxylic acid is warmed to 55° C. and treated with 4.7 g. of dinitrogen tetraoxide in 30 ml. of acetic acid. After 3 hours the mixture is poured into cold water, and the mixture is diluted with diethyl ether. A solid forms and is collected by filtration and dissolved in benzene. The benzene layer is washed with water, cold 0.5 N sodium hydroxide solution, water and saturated sodium chloride solution. The organic layer is dried, then evaporated to provide a residue which is recrystallized from cyclohexane, then from an isopropanol-benzene mixture, then from a dichloroethane-hexane mixture to provide 3-phenyl-2-nitronaphtho-[1,2-b]furan, m.p. 169°–174° C.

| Analysis: | %C | %H | %N |
|---|---|---|---|
| Calculated for C$_{18}$H$_{11}$NO$_3$: | 74.7; | 3.8; | 4.8 |
| Found: | 74.5; | 3.6; | 4.8. |

EXAMPLE 3

Step A. Using the method of Example 1, step A, ethyl 4-hydroxyphenylacetate and α-bromoaceto-2-naphthone are reacted in benzene with potassium carbonate as the catalyst to provide α-[(4-carboethoxymethyl)-phenoxy]aceto-2-naphthone. Recrystallization from an ethyl acetate-hexane mixture provides a light yellow solid.

Step B. A mixture of the product of step A and polyphosphoric acid is reacted using the method of Example 1, step B, to provide 3-(2-naphthyl)-5-carboethoxymethylbenzofuran. The structural assignment is supported by infrared and nuclear magnetic resonance spectral analysis.

Step C. A solution of the product of step B in 100 ml. of ethanol and 100 ml. of 10 percent aqueous sodium hydroxide solution is heated for two hours on a steam bath. The ethanol is removed by evaporation, and the resulting aqueous solution is acidified with 6 N hydrochloric acid. A gummy residue is obtained. Attempted recrystallization from an ethyl acetate-hexane mixture is unsuccessful, and the product 3-(2-naphthyl)-5-carboxymethylbenzofuran is used as is for the next step.

Step D. A solution containing 8 g. of the product of step C in 250 ml. of chloroform is treated with 4 g. of dinitrogen tetraoxide, and the mixture is stirred at about 20° C. for about 16 hours. The chloroform is evaporated to provide a dark residue. The residue is dissolved in 10 percent sodium hydroxide solution, and the solution is acidified with 6 N hydrochloric acid. The residue is collected, washed with water and dissolved in an ethanolchloroform mixture. This mixture is dried and evaporated to provide an oil which is triturated with chloroform to produce a yellow solid. The product is purified by recrystallization from an ethyl acetate-hexane mixture followed by chromatography on silica gel, eluting with chloroform to provide 3-(2-naphthyl)-2-nitro-5-carboxymethylbenzofuran, m.p. 214°–217° C. (dec.).

| Analysis: | %C | %H | %N |
|---|---|---|---|
| Calculated for C$_{20}$H$_{13}$NO$_5$: | 69.2; | 3.8; | 4.0 |
| Found: | 67.3; | 3.7; | 4.5. |

The structural assignment is supported by infrared, nuclear magnetic resonance and mass spectral analysis.

EXAMPLE 4

Step A. Using the method of Example 1, step A, 5-hydroxyindane is reacted with α-chloroacetophenone in benzene in the presence of sodium carbonate to provide α-(5-indanoxy)acetophenone as a yellow solid.

Step B. The product of step A is cyclized in the presence of polyphosphoric acid to provide 6,7-dihydro-3-phenyl-5H-indeno-[5,6-b]furan, m.p. 43°–46° C.

Step C. To a solution of 2.3 g. (0.01 mole) of the product of step B in 100 ml. of chloroform is added 1.8 g. (0.02 mole) of dinitrogen tetraoxide, and the mixture is stirred at about 20° C. for 20 hours. The mixture is evaporated, and the residue is triturated with isopropyl ether to provide a precipitate. The precipitate is separated by filtration and recrystallized from methanol to provide 6,7-dihydro-2-nitro-3-phenyl-5H-indeno-[5,6-b]-furan, m.p. 161°–164° C.

| Analysis: | %C | %H | %N |
|---|---|---|---|
| Calculated for C$_{17}$H$_{14}$O: | 73.1; | 4.7; | 5.0 |
| Found: | 72.3; | 4.6; | 4.9. |

EXAMPLE 5

Step A. The known compound 1-chloro-4-methoxynaphthalene is dissolved in 150 ml. of acetic acid and 150 ml. of 48 percent hydrobromic acid, and the mixture is heated at its reflux temperature for two hours. The mixture is diluted with 200 ml. of water and cooled to provide 1-chloro-4-hydroxynaphthalene as a crystalline solid.

Step B. The product of step A is reacted with α-bromoacetophenone in benzene in the presence of potassium carbonate using the method of Example 1, step A, to provide white crystals of α-(4-chloro-2-naphthoxy)acetophenone after recrystallization from a dichloromethane-petroleum ether mixture.

Step C. The product of step B is reacted in polyphosphoric acid using the method of Example 1, step C, to provide 5-chloro-3-phenylnaphtho-[1,2-b]furan, m.p. 66°–69° C.

| Analysis: | %C | %H | %N |
|---|---|---|---|
| Calculated for C$_{18}$H$_{10}$ClNO$_3$: | 56.8; | 3.1; | 4.3 |
| Found: | 56.7; | 3.1; | 4.4. |

EXAMPLE 6

Step A. To a mixture of 0.5 g. of magnesium and three drops of 1,2-dibromoethane in 75 ml. of tetrahydrofuran at reflux is added 3.4 g. (0.012 mole) of 5-chloro-3-phenylnaphtho-[1,2-b]furan (the compound produced in step C of Example 5 hereof) and 25 ml. of tetrahydrofuran. After heating at reflux for one day, the solution is cooled, and dry carbon dioxide gas is bubbled through the reaction mixture for one hour. The reaction mixture is heated briefly to reflux, then 50 ml. of 6 N hydrochloric acid is added. The reaction mixture is evaporated to provide a residue of 3-phenylnaphtho-[1,2-b]furan-5-carboxylic acid, m.p. 286°–288° C. (dec.). After recrystallization from methanol white crystals are obtained.

Step B. The product of step A is dissolved partially in 125 ml. of hot chloroform, and 1 g. of dinitrogen tetraoxide is added. The mixture is stirred at 20° C. for about one day. The mixture is evaporated to provide a residue which is triturated with isopropyl alcohol. The residue is separated by filtration and recrystallized from acetic acid to provide light yellow crystals of 2-nitro-3-phenylnaphtho-[1,2-b]furan-5-carboxylic acid, m.p. 286°–288° C. (dec.).

| Analysis: | %C | %H | %N |
|---|---|---|---|
| Calculated for C$_{19}$H$_{11}$NO$_5$ · ¼ H$_2$O: | 67.6; | 3.4; | 4.1 |
| Found: | 67.6; | 3.4; | 3.8. |

EXAMPLE 7

Step A. To a solution of several drops of 1,2-dibromoethane in 10 ml. of tetrahydrofuran is added 1.8 g. of magnesium. To this solution is added 16 g. of 3-(4'-bromophenyl)naphtho[1,2-b]furan (the compound produced in step B of Example 1 hereof) in 100 ml. of tetrahydrofuran over a period of 15 minutes. The mixture is heated at its reflux temperature for 16 hours, cooled, and carbon dioxide gas is bubbled into the solution for about one hour. During the last half hour of the addition, the mixture is heated at its reflux temperature. To this mixture is added 50 ml. of 6 N hydrochloric acid. The mixture is stirred for about 20 minutes, then the solvent is evaporated. The residue is recrystallized from acetic acid to provide 3-(4-carboxyphenyl)naphtho-[1,2-b]furan, m.p. 292° C. (dec.).

| Analysis: | %C | %H |
|---|---|---|
| Calculated for C$_{19}$H$_{12}$O$_3$: | 79.1; | 4.2 |
| Found: | 78.5; | 4.2. |

Step B. To a mixture of 4.0 g. of the product of step A in 250 ml. of chloroform is added 4.0 g. of dinitrogen tetraoxide. The mixture is stirred at about 20° C. for 20 hours. The mixture is filtered, and the solid obtained is recrystallized from a mixture of N,N-dimethylformamide and water to provide yellow crystals of 3-(4-carboxyphenyl)-2-nitronaphtho-[1,2-b]furan, m.p. greater than 300° C.

| Analysis: | %C | %H | %N |
|---|---|---|---|
| Calculated for C$_{19}$H$_{11}$NO$_5$: | 68.5; | 3.3; | 4.2 |
| Found: | 68.1; | 3.3; | 4.3. |

EXAMPLE 8

Using the method of Example 1, steps A, B and C and starting with α-naphthol and 4-fluoro-α-bromoacetophenone the product obtained is 3-(4'-fluorophenyl)-2-nitronaphthol-[1,2-b]furan.

EXAMPLE 9

Using the method of Example 5, steps A, B, C and D and starting with 1-fluoro-4-methoxynaphthalene, the product obtained is 5-fluoro-2-nitro-3-phenylnaphtho-[1,2-b]furan.

What is claimed is:

1. A compound of the formula

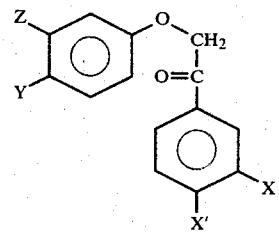

wherein X and X' are individually hydrogen, fluorine, chlorine, bromine or carboxyl or together can complete a benzo ring, Y is hydrogen, fluorine, chlorine, bromine, carboxyl, carboxymethyl or together with Z can form a propylene chain, provided that the compound contains one and only one of the rings including X and X' and Y and Z, and provided further that the compound contains not more than a single carboxyl function.

2. α-(5-Indanoxy)acetophenone according to claim 1.

* * * * *